United States Patent
Wickramathilaka (10) Patent No.: US 10,113,946 B2
(45) Date of Patent: Oct. 30, 2018

(54) ROCK WETTABILITY DETERMINATIONS

(71) Applicant: CONOCOPHILLIPS COMPANY, Houston, TX (US)

(72) Inventor: Siluni Wickramathilaka, Houston, TX (US)

(73) Assignee: CONOCOPHILLIPS COMPANY, Houston, TX (US)

( * ) Notice: Subject to any disclaimer, the term of this patent is extended or adjusted under 35 U.S.C. 154(b) by 186 days.

(21) Appl. No.: 15/191,099

(22) Filed: Jun. 23, 2016

(65) Prior Publication Data

US 2016/0377521 A1  Dec. 29, 2016

Related U.S. Application Data

(60) Provisional application No. 62/184,069, filed on Jun. 24, 2015.

(51) Int. Cl.
| | |
|---|---|
| *G01V 1/40* | (2006.01) |
| *G01N 15/08* | (2006.01) |
| *G01N 13/02* | (2006.01) |
| *G06F 11/30* | (2006.01) |
| *C09K 8/58* | (2006.01) |

(52) U.S. Cl.
CPC .......... *G01N 15/082* (2013.01); *G01N 13/02* (2013.01); *C09K 8/58* (2013.01); *G01N 2013/0208* (2013.01)

(58) Field of Classification Search
None
See application file for complete search history.

(56) References Cited

U.S. PATENT DOCUMENTS

| | | | |
|---|---|---|---|
| 6,178,807 B1 | 1/2001 | Baldwin et al. | |
| 6,415,649 B1 | 7/2002 | Spinler et al. | |
| 6,883,702 B2 * | 4/2005 | Hurlimann | G01V 3/32 |
| | | | 324/303 |
| 2006/0132131 A1* | 6/2006 | Fleury | G01N 15/0826 |
| | | | 324/307 |
| 2012/0136578 A1 | 5/2012 | Ghedan | |
| 2013/0091941 A1 | 4/2013 | Huh | |
| 2013/0325348 A1 | 12/2013 | Valori | |
| 2015/0034307 A1 | 2/2015 | Howard et al. | |

OTHER PUBLICATIONS

Abe, A.A., Relative Permeability and Wettability Implications of Dilute Surfactants at Reservoir Conditions (Thesis 2005).
Al-Mahrooqi, S.H., et al., 2003, An investigation of the effect of wettability on NMR characteristics of sandstone rock and fluid systems, J. Petrol. Sci. Eng., vol. 39, p. 389-398.
Anderson, W.G., "Wettability Literature Survey—Part II: Wettability Measurement", JPT, Nov. 1986, 38, 12, 1246-1262.
(Continued)

*Primary Examiner* — Phuong Huynh
(74) *Attorney, Agent, or Firm* — ConocoPhillips Company (57) ABSTRACT

A new method of assessing wettability of a reservoir rock is provided, using a mineral oil/alkane saturated sample first, a crude oil and water saturated sample equivalent to natural reservoir rock second, and a third crude oil saturated, water free sample, measuring different wettability states and comparing the slopes of all three adjusted values to determine a wettability state for the reservoir rock.

11 Claims, 4 Drawing Sheets

(56) References Cited

OTHER PUBLICATIONS

Behbahani, H.S.Z., Analysis, Scaling and Simulation of Counter-Current Imbibition (Thesis 2004).

Bobek, J.E., et al., "Reservoir Rock Wettability—Its Significance and Evaluation", Trans. AIME, 1958, 213, 155.

Buckley, J.S., "Mechanism and Consequences of Wettability Alteration by Crude Oils", Ph.D. Dissertation, Heriot-Watt University, Edinburgh, United Kingdom, Sep. 1996.

Buckley, J.S., et al., "Mechanisms of Wetting Alteration by Crude Oils", SPEJ, Mar. 1998, 3, 54-61.

Calhoun, J.C., "Criteria for Determining Rock Wettability", Oil & Gas Journal, 1951, 50, 1, 151.

Chen, J, et al., 2006, NMR wettability indices: effect of OBM on wettability and NMR responses, J. Petrol. Sci. Eng., vol 52, p. 161-171.

Cuiec, L.E., "Rock/Crude-Oil Interactions and Wettability: An Attempt to Understand Their Interrelation", SPE 13211 presented at the 1984 Spe Annual Technical Conference and Exhibition, Houston, TX, U.S.A., Sep. 16-19.

Denekas, M.O., Mattax, C.C., & Davis, G.T., "Effect of Crude Oil Components on Rock Wettability", Trans AIME, 1959, 216, 330.

Donaldson, E.G. & Thomas, R.D., "Microscopic Observations of Oil Displacement in Water-Wet and Oil-Wet Systems", SPE 3555, the 46th Annual Fall Meeting, New Orleans, LA, Oct. 3-6, 1971.

Donaldson, E.G., Thomas, R.D., & Lorenz, P.B., "Wettability Determination and Its Effect on Recovery Efficiency", SPE Journal, Mar. 1969, 13.

Fischer, H., & Morrow, N.R., "Scaling of Oil Recovery by Spontaneous Imbibition for Wide Variation in Aqueous Phase Viscosity with Glycerol as the Viscosifying Agent", paper presented at the 8th International Symposium on Reservoir Wettability, May 16-18, 2004, Houston, TX; Journal of Petroleum Science and Engineering, accepted Mar. 7, 2006, 52, 1-4, 35-53.

Freedman, R, et al., 2003, Wettability, saturation and viscosity from NMR measurements, SPEJ, vol. 8, p. 317324.

Garg, A., et al., Experimental and Numerical Studies of One-Dimensional Imbibition in Berea Sandstone.

Howard, J.J., 1998, Quantitative estimates of porous media wellability from proton NMR measurement, Magn. Reson. Imaging, vol. 16, p. 529-533.

Jadhunandan, P. & Morrow, N.R., "Spontaneous Imbibition of Water by Crude Oil/Brine/Rock Systems," In Situ, 1991, 15, 4, 319-345.

Jia, D., Buckley, J.S., & Morrow, N.R., "Control of Core Wettability with Crude Oil", SPE 21041, the SPE International Symposium on Oilfield Chemistry, Anaheim, CA, Feb. 20-22, 1991.

Kamath, I.S.K. & Marsden, S.S., "A Wettability Scale for Porous Media", 1966.

Kazemi, H., Gilman, J.R., & Eisharkawy, A.M., "Analytical and Numerical Solution of Oil Recovery from Fractured Reservoirs with Empirical Transfer Functions", Reservoir Evaluation & Engineering (Society of Petroleum Engineers), May 1992, 219-227.

Kyte, J.R. & Mattax, C.C., "Effect of Reservoir Environment on Water-Oil Displacement", JPT, Jun. 1961, 579-582.

Looyestijn, W.J., 2007, Wettability index determination from NMR logs, presented at SPWLA 48th Annual Logging Symposium, Jun. 3-6, 2007.

Ma, S., Morrow, N.R., & Zhang, X., "Generalized Scaling of Spontaneous Imbibition Data for Strongly Water-Wet Systems", Journal of Petroleum Science and Engineering, 1997, 18, 165-178.

Mason, G., Fischer, H., Morrow, N.R., & Ruth, D.W., "Correlation for the Effect of Fluid Viscosities on Counter-Current Spontaneous Imbibition", Journal of Petroleum Science and Engineering, 2010, 72, 195-205.

Mattax, C.C. & Kyle, J.R., "Imbibition Oil Recovery from Fractured, Water-Drive Reservoirs", Society of Petroleum Engineers Journal, Jun. 1962, 177-184.

Morrow, N.R. & Mason, G., "Recovery of Oil by Spontaneous Imbibition", Current Opinion in Colloid & Interface Science, 2001, 6, 321-337.

Morrow, N.R., "A Review of the Effects of Initial Water Saturation, Pore Structure, and Wettability on Oil Recovery by Naterflooding", Proc. North Sea Oil and Gas Reservoir Seminar, Trondheim (Dec. 2-4, 1985), Graham and Trotman Ltd., London, UK, 1987, 179-191.

Morrow, N.R., "Wettability and Its Effect on Oil Recovery", JPT, Dec. 1990, 42, 12, 1476-1484.

Morrow, N.R., Lim, H.T., & Ward, J.S., "Effect of Crude Oil Induced Wettability on Oil Recovery", SPE Formation Evaluation, Feb. 1986, 89-103.

Raza, S.H., Treiber, L.E., & Archer, D.L., "Wettability of Reservoir Rocks and Its Evaluation", Producers Monthly, 1968, 32, 4, 2-7; abstract only.

SCA2011-24 (2011) Wickramathilaka, S., et al., Magnetic Resonance Imaging of Oil Recovery During Spontaneous Imbibition From Cores With Two-Ends Open Boundary Condition.

Tang, G. Q. & Morrow, N.R., "Salinity, Temperature, Oil Composition and Oil Recovery by Waterflooding", SPE Reservoir Engineering, Nov. 1997, 269-276.

Tie, H. & Morrow, N.R., "Oil Recovery by Spontaneous Imbibition Before and After Wettability Alteration of Three Carbonate Rocks by a Moderately Asphaltic Crude Oil", presented at the 2005 International Symposium of Society of Core Analysts, Toronto, Canada.

Tie, H., Tong, Z., & Morrow, N.R., "The Effect of Different Crude Oil/Brine/Rock Combinations on Wettability through Spontaneous Imbibition", presented at the 2003 International Symposium of the Society of Core Analysts, Pau, France.

Tong, Z. & Morrow, N.R., "Variation in Wettability Behavior of Mixed-Wet Cores Resulting from Probe Oil Solvency and Exposure to Synthetic Oil-Based Mud Emulsifiers", presented at the 8th International Symposium on Reservoir Nettability, Houston, TX, May 16-18, 2004.

Treiber, L.E., Archer, D.L., & Owens., W.W., "A Laboratory Evaluation of the Wettability of Fifty Oil-Producing Reservoirs", SPEJ, Dec. 1972, 531-540.

Xie, X. & Morrow, N.R., "Oil Recovery by Spontaneous Imbibition from Weakly Water-Wet Rocks", Petrophysics, Jul.-Aug. 2001, 42, 4, 313-322.

Zhou, X., Morrow, N.R., & Ma, S., "Interrelationship of Wettability, Initial Water Saturation, Aging Time and Oil Recovery by Spontaneous Imbibition and Water flooding", SPEJ, Jun. 2000, 5, 2, 199-207.

International Search Report for related case, App. No. PCT/US2016/039045, dated Sep. 8, 2016.

* cited by examiner

ROCK WETTABILITY DETERMINATIONS

PRIOR RELATED APPLICATIONS

This application is a non-provisional application which claims benefit under 35 USC § 119(e) to U.S. Provisional Application Ser. No. 62/184,069 filed Jun. 24, 2015, entitled "ROCK WETTABILITY DETERMINATIONS," which is incorporated herein in its entirety.

FEDERALLY SPONSORED RESEARCH STATEMENT

Not applicable.

FIELD OF THE DISCLOSURE

The disclosure generally relates to new methods of measuring the wettability of rock and other materials.

BACKGROUND OF THE DISCLOSURE

Figure 1:
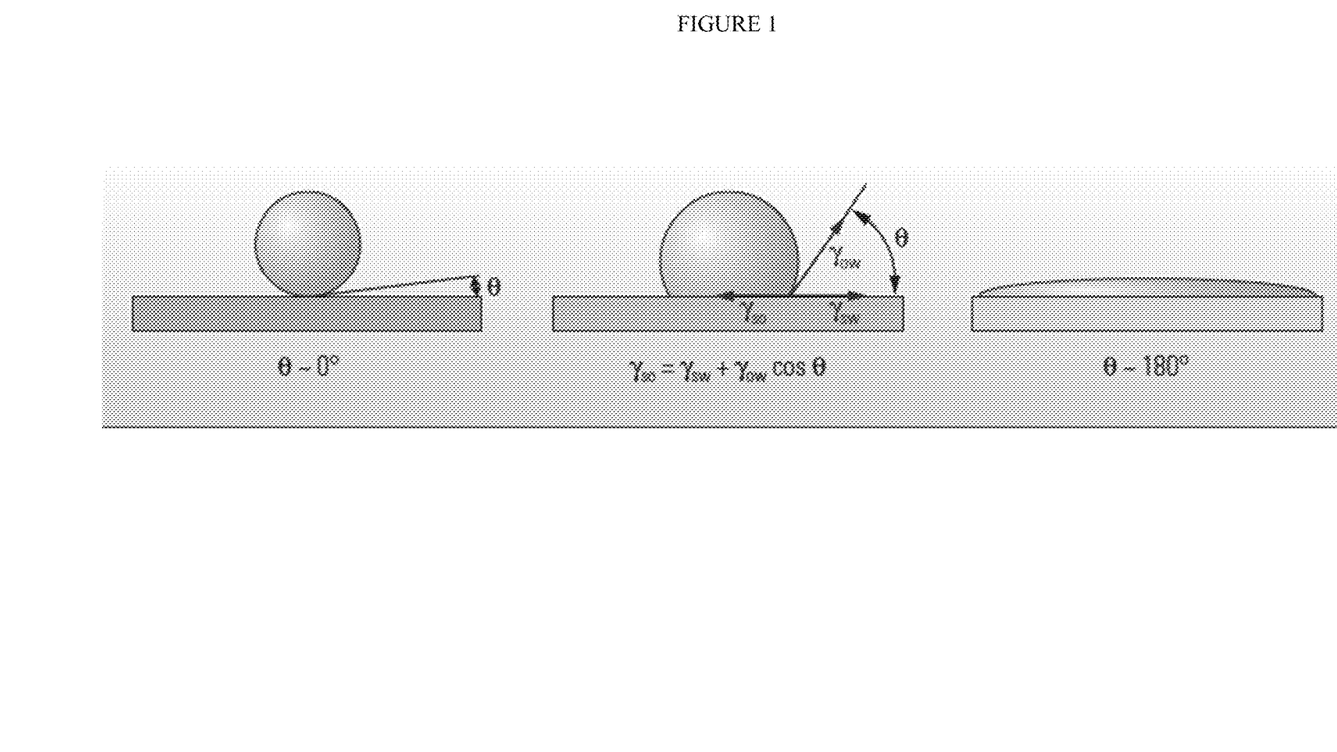
FIG. 1. Illustration of contact angle. An oil drop (green) surrounded by water (blue) on a water-wet surface (left) forms a bead. The contact angle θ is approximately zero. On an oil-wet surface (right), the drop spreads, resulting in a contact angle of about 180°. An intermediate-wet surface (center) also forms a bead, but the contact angle comes from a force balance among the interfacial tension terms, which are $\gamma_{so}$ and $\gamma_{sw}$ for the surface-oil and surface-water terms, respectively, and $\gamma_{ow}$ for the oil-water term.

Wettability describes the preference of a solid to be in contact with one fluid over another based on the balance of surface and interfacial forces. A drop of a preferentially wetting fluid will displace another fluid; at the extreme it will spread over the entire surface. Conversely, if a non-wetting fluid is dropped onto a surface already covered by the wetting fluid, it will bead up, minimizing its contact with the solid. If the condition is neither strongly water-wetting nor strongly oil-wetting, the balance of forces in the oil/water/solid system will result in a contact angle, θ, between the fluids at the solid surface. See e.g., FIG. 1.

In many oilfield applications, wettability is considered in a binary manner—the rock is either water-wet or oil-wet. However, this simplification masks considerable complexity of wetting physics in reservoir rock. In actuality, degrees of intermediate wetting apply along the continuum between strongly oil wetting and strongly water wetting.

Typically, the primary constituents of reservoirs—quartz, carbonate and dolomite—are water-wet prior to oil migration. However, reservoir rocks are complex, including a variety of mineral types with different wettabilities, making the wetting character of the composite rock difficult to describe.

Another complexity is the saturation history of the material, which may influence surface wetting, such that pore surfaces that had been previously contacted by oil may be oil-wet, but those never contacted by oil may be water-wet. Various terms have been used to describe both of these conditions, including mixed-, fractional- and dalmation-wetting.

Herein, the term "mixed-wetting" will be used for any material with inhomogeneous wetting. It is important to note the distinctions between intermediate-wetting (lacking a strong wetting preference) and mixed-wetting (having a variety of preferences, possibly including intermediate-wetting) conditions.

Another important distinction is that a preferentially water-wetting surface can be in contact with oil or gas. Wettability does not describe the saturation state: it describes the preference of the solid for wetting by a certain fluid, given the presence of that preferred wetting fluid. Thus, a water-wet rock can be cleaned, dried and fully saturated with an alkane/mineral oil, while the surfaces in the pores remain water-wet.

Strictly speaking, the term "imbibition" refers to an increase in the saturation of the wetting phase, whether this is a spontaneous imbibition process or a forced imbibition process such as a waterflood in a water-wet material. Conversely, "drainage" refers to an increase in saturation of the nonwetting phase. However, in practice, the term imbibition is used to describe a process with increasing water saturation, and drainage is used to describe a process with increasing oil saturation, and one should be careful when reading the literature to determine which sense is being used.

Several methods are available to measure a reservoir's wetting preference. Oil recovery obtained from imbibition and waterflooding experiments, contact angle measurements and Nuclear Magnetic Resonance (NMR) measurements are the most commonly used methods.

The Amott-Harvey imbibition test is commonly used, for example. A sample at irreducible water saturation and saturated with oil, Swirl', placed into a water-filled imbibition apparatus spontaneously imbibes water over a period of time—at least 10 days, and sometimes much longer. Then the sample is placed in a flow cell and water is injected, with the additional oil recovery noted. The sample is now at residual oil saturation, $S_{or}$, and the process is repeated with an oil-filled imbibition apparatus, and then an oil-flooding apparatus. Separate ratios of spontaneous imbibition to total saturation change for water, $I_w$, and oil, $I_o$, are termed the water and oil imbibition indices, respectively. The Amott-Harvey index is the difference between the water and oil ratios. The result is a number between +1 (strongly water-wetting) and −1 (strongly oil-wetting).

Figure 2:
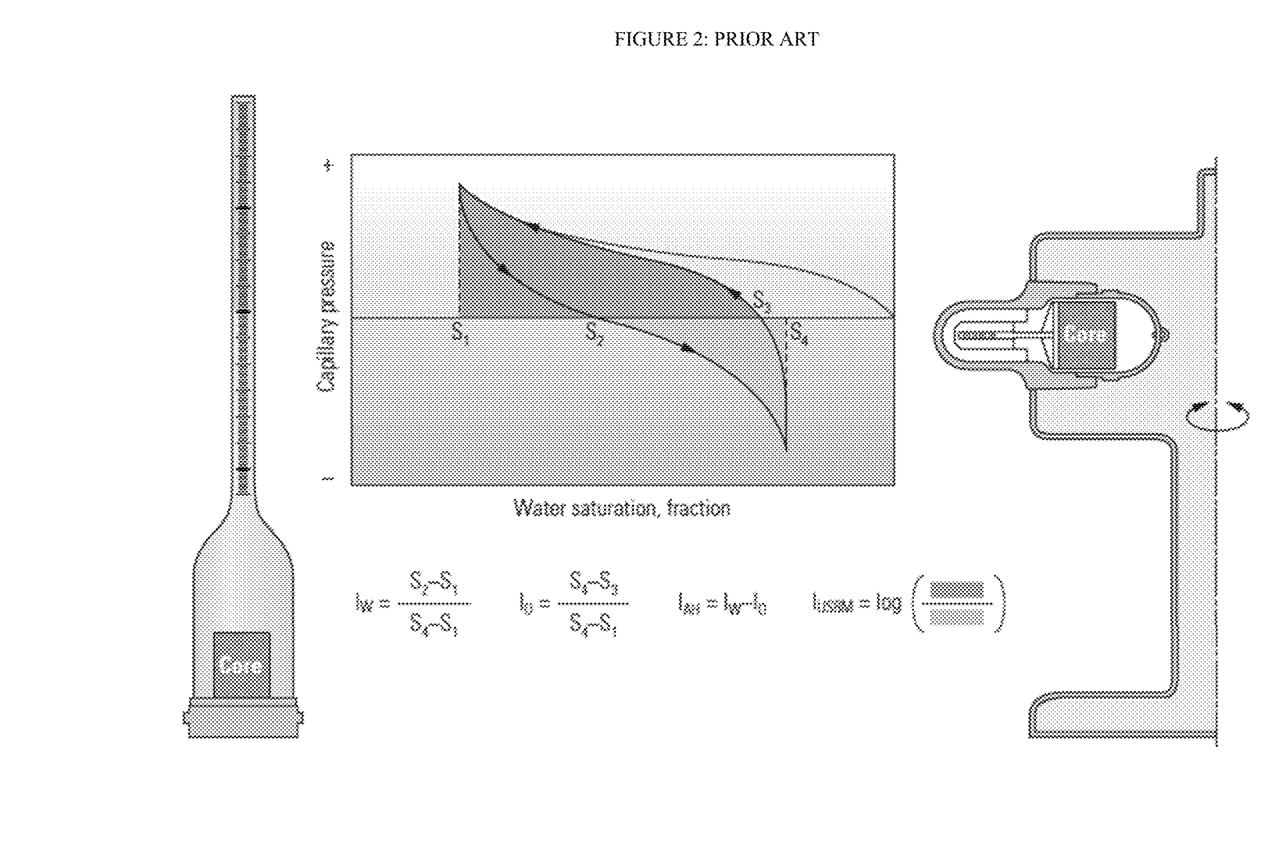

In the US Bureau of Mines (USBM) test, a centrifuge spins the core sample at stepwise increasing speeds. The sample starts at irreducible water saturation and saturated with oil, $S_{wirr}$ in a waterfilled tube. After periods at several spin rates, the sample reaches residual oil saturation, $S_{or}$, and it is placed into an oil-filled tube for another series of measurements. The areas between each of the capillary-pressure curves and the zero capillary-pressure line are calculated, and the logarithm of the ratio of the water-increasing to oil-increasing areas gives the USBM wettability index (FIG. 2). The measurement range extends from +∞ (strongly water wetting) to −∞ (strongly oil wetting), although most measurement results are in a range of +1 to −1. The centrifuge method is fast, but the saturations must be corrected because the centrifuge induces a nonlinear capillary-pressure gradient in the sample.

It is possible to combine the Amott-Harvey and USBM measurements by using a centrifuge rather than flooding with water and oil to obtain the forced flooding states. The Amott-Harvey index is based on the relative change in saturation, while the USBM index gives a measure of the energy needed to make the forced displacement, making them related, but independent indicators of wettability.

NMR has also been used as a tool to measure wettability. The wettability conditions in a porous media containing two or more immiscible fluid phases determine the microscopic fluid distribution in the pore network. NMR measurements are sensitive to wettability because of the strong effect that the solid surface has on promoting magnetic relaxation of the saturating fluid.

The idea of using NMR as a tool to measure wettability was presented by Brown and Fatt in 1956. Their theory was based on the hypothesis that molecular movements are slower in the bulk liquid than at the solid-liquid interface. In this solid-liquid interface the diffusion coefficient is reduced, which correspond to a zone of higher viscosity. In this higher viscosity zone, the magnetically aligned protons can more easily transfer their energy to their surroundings. The magnitude of this effect depends upon the wettability characteristics of the solid with respect to the liquid in contact with the surface.

These methods only measure wettability as a function of the final oil recovery or saturation and therefore, represent only the displacement efficiency. However, oil production rates are also an important factor in evaluating a reservoir and it has been observed that oil production rates from rocks with different wettabilities vary. It has also been observed that the final oil recovery may vary for rocks with similar wettability conditions. Furthermore, other popular methods of wettability measurement, such as measuring contact angle against a known surface, do not accurately predict the wettability of a heterogeneous reservoir rock.

Therefore, what is needed in the art are better methods of assessing wettability, in particular methods that allow for corrections for variations in core properties, sample size and geometry.

SUMMARY OF THE DISCLOSURE

A spontaneous imbibition experiment provides the amount of oil recovered over time due to naturally occurring capillary forces. Various researchers have established correlations for sandstones and carbonates that could then be used to correct for variations in core properties, sample size and geometry in an imbibition experiment. The rock type also plays a significant role in determining the final oil recovery and oil production rates. The adjusted spontaneous imbibition curves using the established correlations are then used to estimate the oil production rates/production curve slopes. These slopes could then be compared to a base case to determine the wettability of that particular rock.

A clean core sample that has not come into contact with any crude oil (generally, outcrop rocks) is considered to have closer to Very Strongly Water-Wet (VSWW) conditions. Water-wet rocks are generally thought to have faster imbibition oil production rates than mixed-wet and oil-wet rock samples. So it is suggested that for each rock sample of interest, the rock sample (reservoir rock) is well cleaned so that the core could be used to set up a VSWW condition experiment. Outcrop rocks could also be used without rigorous cleaning steps since they generally have not been contacted by any crude oil.

The cleaned sample is then completely saturated with a mineral oil that does not have any polar contaminants (the mineral oil should be cleaned with activated alumina and silica gel). A spontaneous imbibition experiment is conducted and an oil recovery curve is obtained.

This recovery curve is then adjusted using a selected dimensionless time correlation or a square root of time. By using these correlations, different core samples can be accurately compared by scaling the differences in rock properties, etc., among the various samples that were used for the tests. The core sample that was saturated with the mineral oil/alkane could be considered as a VSWW condition. When saturated completely with crude oil, the sample could be considered as close to oil-wet condition. Any other saturation in-between these two conditions could be considered as mixed-wet. The difference in results between the VSWW and oil-wet conditions would be analyzed to determine the state of the mixed wettability (more water-wet or more oil-wet). The VSWW condition rocks would show the fastest imbibition rates and the oil-wet rocks would show the slowest imbibition rates.

There are different variations of dimensionless time correlations used to scale spontaneous imbibition results. One correlation that applies to a wide range of data is illustrated here:

$$t_D = t \sqrt{\frac{k}{\phi}} \frac{\sigma}{\sqrt{\mu_w \mu_o}} \frac{1}{L^2}$$

where $t_D$ is the dimensionless time, t is the imbibition time, k is the permeability of the rock, $\phi$ is the porosity of the rock, $\sigma$ is the interfacial tension between water and oil, $\mu_w$ is the water viscosity, $\mu_o$ is the oil viscosity, and L is the characteristic length. The most commonly used geometry and boundary condition in the laboratory studies is the cylindrical core samples with all of the faces open to flow. For core samples with similar geometry/shape and boundary condition, the characteristic core length, L, could be defined as following:

$$L = \frac{dl}{2\sqrt{2l^2 + d^2}}$$

where d is the diameter of the cylindrical core and l is the length of the core sample.

The desired rock saturated with crude oil and initial water saturation can then be used to conduct another spontaneous imbibition experiment. The obtained oil recovery curve is again modified using an appropriate imbibition correlation. If possible, another crude oil and reservoir/outcrop rock should be performed with only using the crude oil (without any initial/connate water in the core sample).

The slopes of the imbibition rates are then estimated for the three sets of results and could be compared against one another to evaluate the wettability of the reservoir rock samples.

Figure 3:
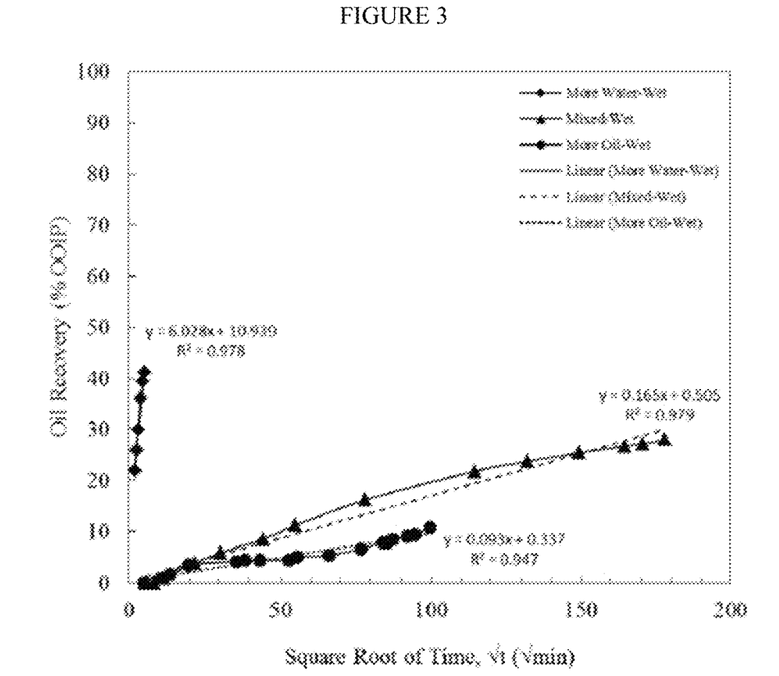
FIG. 3 a graph illustrating the proposed method, wherein the % Original Oil in Place (OOIP) is plotted against square root of time.
Figure 4:
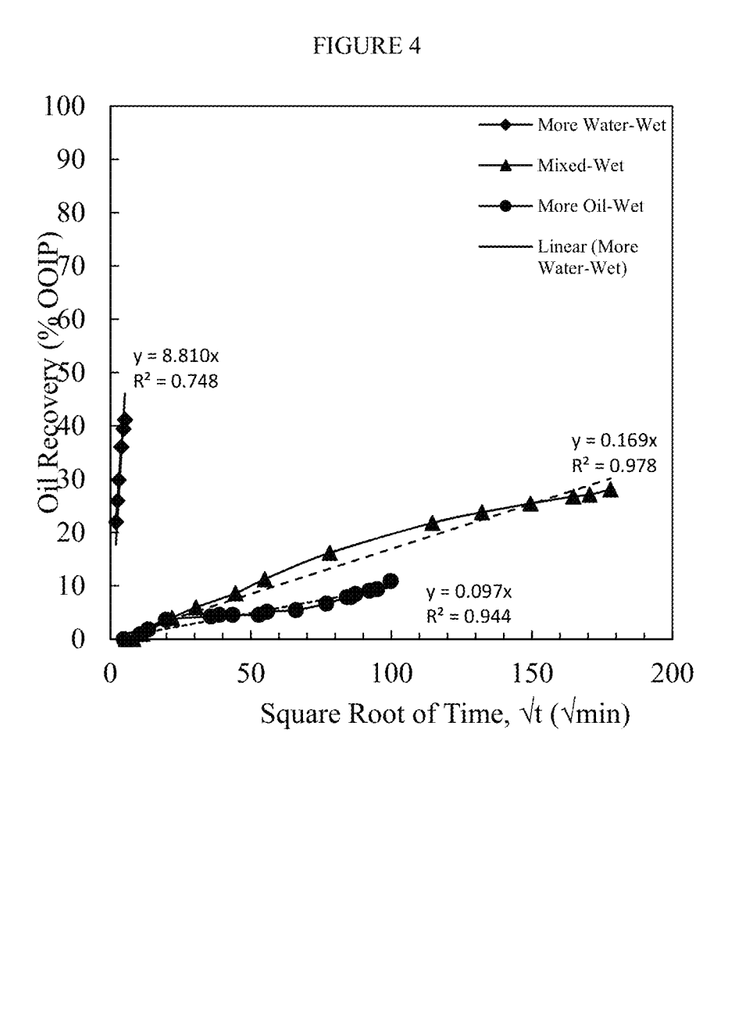
FIG. 4 is the graph from FIG. 3, with intercepts for each curve adjusted to zero.

For example, set the intercept of the curves in FIG. 3 equal to zero, as shown in FIG. 4. Obtain the slopes of these adjusted curves. Obtain the slopes of the VSWW and oil-wet curves first, followed by the slopes of the other curves. Divide the slope of the imbibition curve of the core sample of interest by the addition of the slopes of the curves for VSWW and oil-wet core sample imbibition curves. This would give the wettability index calculated by using imbibition curves. The index is between "0" and "1". If the calculated value is less than 0.25, the core could be considered as more oil-wet and if the value is greater than 0.75, the core could be considered as more water-wet. The values in-between could be considered as mixed-wet.

The most well established base case for a spontaneous imbibition oil production curve is a well known Berea sandstone curve. This outcrop sandstone rock has been widely accepted as a water-wet rock in the industry. Therefore, the base case experiment for comparison with a desired rock could be run using a Berea sandstone core with a relatively lower viscosity mineral oil if other outcrop rocks are not available.

Laboratory experiments are often carried out without any knowledge of the wettability of the studied rocks, depending on the type of experiment. Various methods are used to set up a desired oil/brine/rock system. An understanding of the rock wettability of the core sample is necessary to accurately evaluate the oil recovery and production rate results since both of these depend on the rock wettability. Rock wettability could also vary based on the methodology used to prepare the rock sample. A new approach of measuring wettability is suggested using spontaneous imbibition experiments.

As used herein, "imbibition" can be defined as the process of absorbing a wetting phase into a porous rock or the capillary suction of a wetting phase into a porous medium. It is also defined as the intake of a wetting phase into pore spaces of a porous media by capillary forces. The opposite of imbibition phenomena is the drainage process.

The invention includes any one or more of the following embodiments, in any combination(s) thereof:

In one embodiment, the wettability of a reservoir rock is determined by cleaning a first sample of reservoir rock thoroughly; saturating the clean sample with a mineral oil or alkane and performing a first imbibition experiment, and plotting a first oil recovery plot against dimensionless time or square root of time; obtaining a second sample of the reservoir rock that contains oil and water in a natural state and performing a second imbibition experiment; and plotting a second oil recovery plot against dimensionless time or square root of time; and obtaining a third sample of the reservoir rock and cleaning said third sample thoroughly; saturating the third sample with the crude oil from the reservoir and performing a third imbibition experiment; and plotting a third oil recovery plot against dimensionless time or square root of time; then adjusting the first, second and third oil recovery plots to a y intercept of zero; and estimating the slopes of the adjusted first (m1), second (m2) and third (m3) oil recovery plots; finally calculating a wettability index using: wettability index=mx/(mVSWW+mOW).

The sample may be an outcrop rock representative of the reservoir. The first and third samples are cleaned rock from said reservoir. This method works well with Berea sandstone or other outcrop sandstone representative of the reservoir. This method also works well when the reference sample for first and third samples is an outcrop carbonate, limestone, dolomite or chalk representative of the reservoir. In other examples, the reference sample for only the first sample can be Berea sandstone, other outcrop sandstone, outcrop carbonate, limestone, dolomite or chalk representative of the reservoir and the third sample may be a cleaned reservoir rock sample. In one example, the first and third samples may be Berea sandstone or other outcrop sandstone while the second sample is a sandstone reservoir. In yet another example, the first and third samples may be outcrop carbonate, limestone, dolomite, chalk or reservoir rock itself while the second sample is a carbonate type reservoir.

The mineral oil or alkane used to saturate the first sample may be a low viscosity mineral oil cleaned with activated alumina and silica gel, an n-alkane, a kerosene or an apolar model oil. Additionally, the crude oil used to saturate the third sample may be the crude oil from the reservoir or a crude oil representative of crude oil from the reservoir. The brine used to immerse the core samples in imbibition studies may be synthetic reservoir brine or reservoir brine obtained from the reservoir.

There are a variety of imbibition experiments used to measure the imbibition including the methods depicted in FIG. 2. Additional imbibition experiments include high temperature imbibition, including glass cell, dual cell, and metal cell apparatus which may be used at higher temperatures or for different solutions. Alternatively, imbibition experiments may use core samples saturated with brine, oil, brine and oil, or other solutions. In another embodiment, the core is saturated with brine and oil, the prepared core is then placed in the imbibition cell, the cell is filled with a brine solution and the apparatus assembled. The brine is imbibed into the core and oil is expelled out, the recover oil volume is then accurately measured.

Dimensionless time ($t_D$) is calculated through one or more dimensionless imbibition time equations where parameters including reservoir permeability, porosity, fluid interfacial tension, viscosity, core sample length, and the like are used to determine a dimensionless time. A variety of different dimensionless time correlations available in the literature. One correlation that applies to a wide range of data is:

$$t_D = t \sqrt{\frac{k}{\phi}} \frac{\sigma}{\sqrt{\mu_w \mu_o}} \frac{1}{L^2}$$

where $t_D$ is the dimensionless time, t is the imbibition time, k is the permeability of the rock, $\phi$ is the porosity of the rock, $\sigma$ is the interfacial tension between water and oil, $\mu_w$ is the water viscosity, $\mu_o$ is the oil viscosity, and L is the characteristic length. The most commonly used geometry and boundary condition in the laboratory studies is the cylindrical core samples with all of the faces open to flow.

Very Strongly Water-Wet (VSWW) is the wettability condition in which the rock has a high preference towards water-wetness. In other words, the rock prefers water over oil and therefore, the brine/water will imbibe into the core very quickly. This type of a wettability condition is setup in the laboratory by completely saturating the core with a mineral oil, alkane or other mineral oil hydrocarbon.

Mineral oils are commercially available in a variety of viscosities and purities. Mineral oil is typically a transparent, colorless oil composed mainly of alkanes (typically 15 to 40 carbons) and cyclic paraffins. Low viscosity mineral oils range in viscosity from less than 5 centipoise (cP) down to about 1 cP, including commercially available mineral oils with a viscosity of about 4.2 cP, 4 cP, 3.8 cP, 3.6 cP, 3.4 cP, 3.2 cP, 3.0 cP, 2.8 cP, 2.6 cP, 2.4 cP, 2.2 cP, 2.0 cP, 1.8 cP, 1.6 cP, 1.4 cP, 1.2 cP, 1.0 cP, and mixtures thereof. Mineral oil typically includes a mixture of oils and may have differing viscosities at different temperatures, this relationship is well understood and quantified for mineral oils.

Brine is any saline aqueous solution containing water and salts. Seawater is a commonly used brine composition with about 35,00 ppm (mg/L) Total Dissolved Solids (TDS) that may contain sodium chloride, potassium chloride, magnesium chloride, calcium chloride, and other salts.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, and the like.

The following abbreviations are used herein:

| ABBREVIATION | TERM |
|---|---|
| OOIP | Original Oil in Place |
| VSWW | Very Strongly Water-Wet |
| NMR | Nuclear Magnetic Resonance |
| USBM | US Bureau of Mines |
| OW | Oil-Wet |

BRIEF DESCRIPTION OF THE DRAWINGS

FIG. 2: PRIOR ART. Measurement of core wettability. An imbibition cell contains a sample at $S_{wirr}$ in water (left). Expelled oil collects at the top of a graduated burette. A similar cell turned upside down can measure oil imbibition, starting at $S_{or}$. In a centrifuge, the graduated tube is at a larger radius than the core for collecting water (right), and in an opposite configuration to collect oil. The measurements are illustrated on a capillary-pressure curve (center). Spontaneous water imbibition is from S1, which is $S_{wirr}$ to S2 at zero capillary pressure. The core is waterflooded or spun in a centrifuge, moving along the negative capillary-pressure curve to S4. Spontaneous oil imbibition is from S4 to S3, and then an oilflood takes the sample back to S1, assuming there was no wettability change due to flooding. The imbibition index is the ratio of spontaneous saturation change to spontaneous plus driven saturation change, separately determined for water, $I_w$, and oil, $U_o$. The Amott-Harvey index is $I_w$-$I_o$. The USBM index uses the areas under the positive and negative capillary-pressure curves. This index is the logarithm of the ratio of the areas.

DETAILED DESCRIPTION

The present invention is exemplified with respect to an outcrop rock. However, this is exemplary only, and the invention can be broadly applied to any reservoir rock or complex material. The following examples are intended to be illustrative only, and not unduly limit the scope of the appended claims.

The disclosure provides a novel method of assessing wettability of reservoir rocks.

The more water-wet curve was obtained by an imbibition experiment where the core was fully saturated by a mineral oil/alkane (such as n-decane). The more oil-wet curve was obtained by an imbibition experiment where the core was fully saturated by a crude oil.

The mixed-wet curve was obtained by saturating the curve with an irreducible/connate water saturation and a crude oil. Since the core samples used for the experiments here had similar core properties, a dimensionless time correlation was not used. Instead, a square root of time was used to plot oil recovery as a % OOIP for comparison. This is another way to correlate imbibition data. The curve should be a straight line. The equations used were:

$$\frac{\text{Recovered Oil}}{\text{Original Oil In Place}} * 100\%$$

where % OOIP Recovered is 100 times the Recovered Oil divided by the Initial Oil In Place.

If core samples with different core properties/reservoir rocks are used instead, it is suggested to plot oil recovery against a dimensionless time. As noted above, there are different variations of dimensionless time correlations available in the literature. One correlation that applies to a wide range of data:

$$t_D = t \sqrt{\frac{k}{\phi}} \frac{\sigma}{\sqrt{\mu_w \mu_o}} \frac{1}{L^2}$$

where $t_D$ is the dimensionless time, t is the imbibition time, k is the permeability of the rock, φ is the porosity of the rock, σ is the interfacial tension between water and oil, $\mu_w$ is the water viscosity, $\mu_o$ is the oil viscosity, and L is the characteristic length. The most commonly used geometry and boundary condition in the laboratory studies is the cylindrical core samples with all of the faces open to flow.

For core samples with similar geometry/shape and boundary condition, the characteristic core length, L, could be defined as following:

$$L = \frac{dl}{2\sqrt{2l^2 + d^2}}$$

where d is the diameter of the cylindrical core and l is the length of the core sample.

As noted above, our data was plotted as square root of time versus oil recovery as a % OOIP in FIG. 3. Next, the intercept of each of the curves in FIG. 3 is set to zero, as shown in FIG. 4, and slopes obtained for these adjusted curves. Obtain the slopes of the VSWW and oil-wet curves first, followed by the slopes of the other curves. Divide the slope of the imbibition curve of the core sample of interest by the addition of the slopes of the curves for VSWW and oil-wet core sample imbibition curves, per the following equation:

wettability index=$m_x/[m_{vsww}+m_{ow}]$ where $m_x$ is the slope of the imbibition curve from the core sample of interest, $m_{vsww}$ is the slope of the imbibition curve of a VSWW core sample and mow is the slope of the imbibition curve of an oil-wet core sample. The wettability index may be calculated by using imbibition curves. For example, using the data in FIG. 4, the calculated wettability index was 0.169/(8.81+0.097)=0.169/8.907=0.019

The index is between "0" and "1". If the calculated value is less than 0.25, the core could be considered as more oil-wet and if the value is greater than 0.75, the core could be considered as more water-wet. The values in-between could be considered as mixed-wet. The rock tested herein is more oil-wet.

The following references are incorporated by reference in their entirety for all purposes.

Abe, A. A., Relative Permeability And Wettability Implications Of Dilute Surfactants At Reservoir Conditions (Thesis 2005).

Al-Mahrooqi, S. H., et al., 2003, An investigation of the effect of wettability on NMR characteristics of sandstone rock and fluid systems, J. Petrol. Sci. Eng., vol. 39, p. 389-398.

Anderson, W. G., "Wettability Literature Survey—Part II: Wettability Measurement", JPT, November 1986, 38, 12, 1246-1262.

Behbahani, H. S. Z., Analysis, Scaling and Simulation of Counter-Current Imbibition (Thesis 2004).

Bobek, J. E., et al., "Reservoir Rock Wettability—Its Significance and Evaluation", Trans. AIME, 1958, 213, 155.

Buckley, J. S., "Mechanism and Consequences of Wettability Alteration by Crude Oils", Ph.D. Dissertation, Heriot-Watt University, Edinburgh, United Kingdom, September 1996.

Buckley, J. S., et al., "Mechanisms of Wetting Alteration by Crude Oils", SPEJ, March 1998, 3, 54-61.

Calhoun, J. C., "Criteria for Determining Rock Wettability", Oil & Gas Journal, 1951, 50, 1, 151.

Chen, J, et al., 2006, NMR wettability indices: effect of OBM on wettability and NMR responses, J. Petrol. Sci. Eng., vol 52, p 161-171.

Cuiec, L., "Wettability and Oil Recoveries", North Sea Oil and Gas Reservoirs, The Norwegian Institute of Technology (Graham and Trotman, 1987), 193-207.

Cuiec, L. E., "Evaluation of Reservoir Wettability and Its Effect on Oil Recovery", Interfacial Phenomena in Petroleum Recovery, Ed. N. R. Morrow, Marcel Dekker, Inc., New York, 1991, 319-375.

Cuiec, L. E., "Rock/Crude-Oil Interactions and Wettability: An Attempt to Understand Their Interrelation", SPE 13211 presented at the 1984 SPE Annual Technical Conference and Exhibition, Houston, Tex., U.S.A., September 16-19.

Denekas, M. O., Mattax, C. C., & Davis, G. T., "Effect of Crude Oil Components on Rock Wettability", Trans AIME, 1959, 216, 330.

Donaldson, E. C. & Thomas, R. D., "Microscopic Observations of Oil Displacement in Water-Wet and Oil-Wet Systems", SPE 3555, the 46$^{th}$ Annual Fall Meeting, New Orleans, La., Oct. 3-6, 1971.

Donaldson, E. C., Thomas, R. D., & Lorenz, P. B., "Wettability Determination and Its Effect on Recovery Efficiency", SPE Journal, March 1969, 13.

Fischer, H., & Morrow, N. R., "Scaling of Oil Recovery by Spontaneous Imbibition for Wide Variation in Aqueous Phase Viscosity with Glycerol as the Viscosifying Agent", paper presented at the 8$^{th}$ International Symposium on Reservoir Wettability, May 16-18$^{th}$, 2004, Houston, Tex.; Journal of Petroleum Science and Engineering, accepted 7 Mar., 2006, 52, 1-4, 35-53.

Freedman, R, et al., 2003, Wettability, saturation and viscosity from NMR measurements, SPEJ, vol. 8, p. 317324.

Frehse, W., "Method for Evaluation of the Wettability of Reservoir Rocks" (in German), Z. Fur.Aug. Geol., 1973, 19, 2, 86-88.

Garg, A., et al., Experimental and Numerical Studies of One-Dimensional Imbibition in Berea Sandstone.

Howard, J. J., 1998, Quantitative estimates of porous media wettability from proton NMR measurement, Magn. Reson. Imaging, vol. 16, p. 529-533.

Jadhunandan, P. & Morrow, N. R., "Spontaneous Imbibition of Water by Crude Oil/Brine/Rock Systems," In Situ, 1991, 15, 4, 319-345.

Jia, D., Buckley, J. S., & Morrow, N. R., "Control of Core Wettability with Crude Oil", SPE 21041, the SPE International Symposium on Oilfield Chemistry, Anaheim, Calif., Feb. 20-22, 1991.

Kamath, I. S. K. & Marsden, S. S., "A Wettability Scale for Porous Media", 1966.

Kazemi, H., Gilman, J. R., & Eisharkawy, A. M., "Analytical and Numerical Solution of Oil Recovery from Fractured Reservoirs with Empirical Transfer Functions", Reservoir Evaluation & Engineering (Society of Petroleum Engineers), May 1992, 219-227.

Kennedy, H. T. Burja, E. O., & Boykin, R. S., "An Investigation of the Effect of Wettability on the Recovery of Oil by Waterflooding", Journal of Physical Chemistry, 1955, 29, 867.

Kinney, P. T. & Nielsen, R. F., "Wettability in Oil Recovery", World Oil, April 1951, 145.

Kyte, J. R. & Mattax, C. C., "Effect of Reservoir Environment on Water-Oil Displacement", JPT, June 1961, 579-582.

Looyestijn, W. J., 2007, Wettability index determination from NMR logs, presented at SPWLA 48th Annual Logging Symposium, Jun. 3-6, 2007.

Ma, S., Morrow, N. R., & Zhang, X., "Generalized Scaling of Spontaneous Imbibition Data for Strongly Water-Wet Systems", Journal of Petroleum Science and Engineering, 1997, 18, 165-178.

Mason, G., Fischer, H., Morrow, N. R., & Ruth, D. W., "Correlation for the Effect of Fluid Viscosities on Counter-Current Spontaneous Imbibition", Journal of Petroleum Science and Engineering, 2010, 72, 195-205.

Mattax, C. C. & Kyte, J. R., "Imbibition Oil Recovery from Fractured, Water-Drive Reservoirs", Society of Petroleum Engineers Journal, June 1962, 177-184.

Morrow, N. R. & Mason, G., "Recovery of Oil by Spontaneous Imbibition", Current Opinion in Colloid & Interface Science, 2001, 6, 321-337.

Morrow, N. R., "A Review of the Effects of Initial Water Saturation, Pore Structure, and Wettability on Oil Recovery by Waterflooding", Proc. North Sea Oil and Gas Reservoir Seminar, Trondheim (Dec. 2-4, 1985), Graham and Trotman Ltd., London, UK, 1987, 179-191.

Morrow, N. R., "Wettability and Its Effect on Oil Recovery", JPT, December 1990, 42, 12, 1476-1484.

Morrow, N. R., Lim, H. T., & Ward, J. S., "Effect of Crude Oil Induced Wettability on Oil Recovery", SPE Formation Evaluation, February 1986, 89-103.

Raza, S. H., Treiber, L. E., & Archer, D. L., "Wettability of Reservoir Rocks and Its Evaluation", Producers Monthly, 1968, 32, 4, 2-7.

SCA2011-24 (2011) Wickramathilaka, S., et al., Magnetic Resonance Imaging Of Oil Recovery During Spontaneous Imbibition From Cores With Two-Ends Open Boundary Condition.

Tang, G. Q. & Morrow, N. R., "Effect of Temperature, Salinity and Oil Composition on Wetting Behavior and Oil Recovery by Waterflooding", SPE Reservoir Engineering, November 1997, 269-276.

Tie, H. & Morrow, N. R., "Oil Recovery by Spontaneous Imbibition Before and After Wettability Alteration of Three Carbonate Rocks by a Moderately Asphaltic Crude Oil", presented at the 2005 International Symposium of Society of Core Analysts, Toronto, Canada.

Tie, H., Tong, Z., & Morrow, N. R., "The Effect of Different Crude Oil/Brine/Rock Combinations on Wettability through Spontaneous Imbibition", presented at the 2003 *International Symposium of the Society of Core Analysts*, Pau, France.

Tong, Z. & Morrow, N. R., "Variation in Wettability Behavior of Mixed-Wet Cores Resulting from Probe Oil Solvency and Exposure to Synthetic Oil-Based Mud Emulsifiers", presented at the 8*th International Symposium on Reservoir Wettability*, Houston, Tex., 16-18 May, 2004.

Treiber, L. E., Archer, D. L., & Owens., W. W., "A Laboratory Evaluation of the Wettability of Fifty Oil-Producing Reservoirs", *SPEJ*, December 1972, 531-540.

U.S. Pat. No. 6,178,807 U.S. Pat. No. 6,415,649 Method for laboratory measurement of capillary pressure in reservoir rock U.S. Pat. No. 6,883,702 Method and apparatus for NMR measurement of wettability Xie, X. & Morrow, N. R., "Oil Recovery by Spontaneous Imbibition from Weakly Water-Wet Rocks", *Petrophysics*, July-August 2001, 42, 4, 313-322.

Zhou, X., Morrow, N. R., & Ma, S., "Interrelationship of Wettability, Initial Water Saturation, Aging Time and Oil Recovery by Spontaneous Imbibition and Waterflooding", *SPEJ*, June 2000, 5, 2, 199-207.

The invention claimed is:

1. A method of assessing wettability of a reservoir rock, comprising:
   a) obtaining a first sample of a reservoir rock from a reservoir and cleaning said first sample;
   b) saturating said first sample with a mineral oil or alkane and performing a first imbibition experiment;
   c) plotting a first oil recovery plot against dimensionless time or square root of time;
   d) obtaining a second sample of said reservoir rock that contains oil and water in a natural state and performing a second imbibition experiment;
   e) plotting a second oil recovery plot against dimensionless time or square root of time;
   f) obtaining a third sample of said reservoir rock and cleaning said third sample;
   g) saturating said third sample with the crude oil of said reservoir and performing a third imbibition experiment;
   h) plotting a third oil recovery plot against dimensionless time or square root of time;
   i) adjusting said first, second and third oil recovery plots to a y intercept of zero; and
   j) estimating the slopes of the adjusted first ($m_1$), second ($m_2$) and third ($m_3$) oil recovery plots;
   k) calculating a wettability index using:

$$\text{wettability index} = m_x/(m_{vsww} + m_{ow})$$

where $m_x$ is the slope of the imbibition curve from the core sample of interest $m_1$, $m_2$, or $m_3$, $m_{vsww}$ is the slope of the imbibition curve of a Very Strongly Water-Wet (VSWW) core sample and $m_{ow}$ is the slope of the imbibition curve of an oil-wet (ow) core sample.

2. The method of claim 1, wherein said first sample is outcrop rock representative of the said reservoir.

3. The method of claim 1, wherein said first and third samples are cleaned rock from said reservoir.

4. The method of claim 1, wherein said reference sample for first and third samples is Berea sandstone or other outcrop sandstone representative of the said reservoir.

5. The method of claim 1, wherein said reference sample for first and third samples is an outcrop carbonate, limestone, dolomite or chalk representative of the said reservoir.

6. The method of claim 1, wherein said reference sample for only the first sample is Berea sandstone, other outcrop sandstone, outcrop carbonate, limestone, dolomite or chalk representative of the said reservoir and the third sampled is a cleaned reservoir rock sample.

7. The method of claim 1, wherein the first and third samples are Berea sandstone outcrop or other outcrop sandstone where the second sample is a sandstone reservoir.

8. The method of claim 1, wherein the first and third samples are outcrop carbonate, limestone, dolomite, chalk or reservoir rock itself where the second sample is a carbonate type reservoir.

9. The method of claim 1, wherein the mineral oil or alkane used to saturate the first sample is a low viscosity mineral oil cleaned with activated alumina and silica gel, an n-alkane, a kerosene or an apolar model oil.

10. The method of claim 1, wherein the crude oil used to saturate the third sample is the crude oil from said reservoir or a crude oil representative of said reservoir.

11. The method of claim 1, where in the brine used to immerse the core samples in imbibition studies is synthetic reservoir brine or reservoir brine obtained from said reservoir.

* * * * *